United States Patent

Raspanti

[11] Patent Number: 5,278,310
[45] Date of Patent: Jan. 11, 1994

[54] METHYL PIPERIDINE DERIVATIVES OF CINNAMIC ACIDS, BENZOIC ACIDS, BENZOAZOLS AND BENZOPHENONES USEFUL AS SKIN ANTI-AGING COMPOUNDS

[75] Inventor: Giuseppe Raspanti, Bergamo, Italy

[73] Assignee: Sigma Prodotti Chimici S.p.A., Milan, Italy

[21] Appl. No.: 889,951

[22] Filed: May 29, 1992

[30] Foreign Application Priority Data

Jun. 4, 1991 [IT] Italy ............. MI91 A001520

[51] Int. Cl.$^5$ ............... C07D 211/44; A61K 31/445
[52] U.S. Cl. ..................... 546/222; 424/59; 424/60; 424/401
[58] Field of Search ............ 546/222; 514/327; 424/60, 59, 401

[56] References Cited

U.S. PATENT DOCUMENTS 4,289,686 9/1981 Rody et al. ............... 546/222 X

OTHER PUBLICATIONS

Chem. Abs.; 107:24192t; Volkotrub et al.; 1987.

*Primary Examiner*—Marianne M. Cintins
*Assistant Examiner*—Michael B. Hydorn
*Attorney, Agent, or Firm*—Griffin Butler Whisenhunt & Kurtossy

[57] ABSTRACT

Free radical deactivating 4- or 1,4-substituted, 2,2,6,6-tetramethyl piperidines are condensed with UV absorbing cinnamic acids or benzoic acids or benzoazols or benzophenones to produce skin anti-aging compounds and compositions which have both free radical deactivation and UV absorbing properties.

2 Claims, No Drawings

METHYL PIPERIDINE DERIVATIVES OF CINNAMIC ACIDS, BENZOIC ACIDS, BENZOAZOLS AND BENZOPHENONES USEFUL AS SKIN ANTI-AGING COMPOUNDS

The present invention relates to compounds of general formula (I)

$$(U)_nA \quad (I)$$

in which A is a group of formulae (II)-(V)

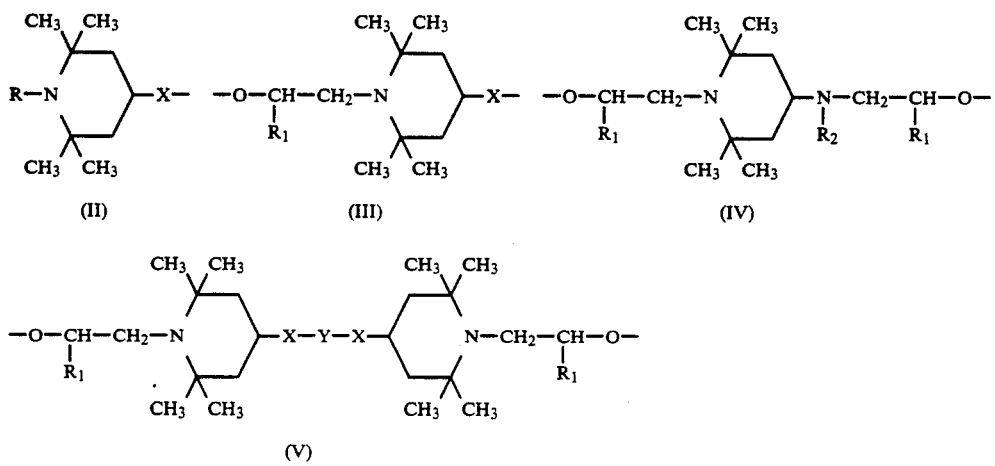

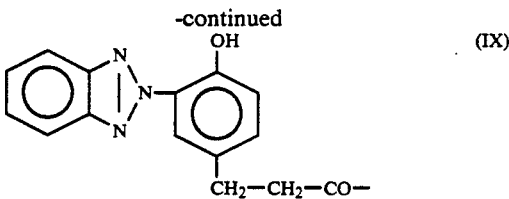

in which R is hydrogen, $C_1$-$C_{12}$ alkyl, $C_2$-$C_4$ hydroxyalkyl or a polyoxyethylene residue containing from 2 to 20 oxyethylene units, X is oxygen or $>NR_2$, in which $R_2$ is hydrogen, a $C_1$-$C_{12}$ alkyl or $C_5$-$C_8$ cycloalkyl group, $R_1$ is hydrogen, methyl or ethyl, Y is $C_2$-$C_6$ alkylene, a diacyl residue deriving from carbonic acid or from a dicarboxylic organic acid or a dicarbamoyl residue deriving from a diisocyanate, n can be the integer 1 or 2, U is a group of formulae (VI)-(IX)

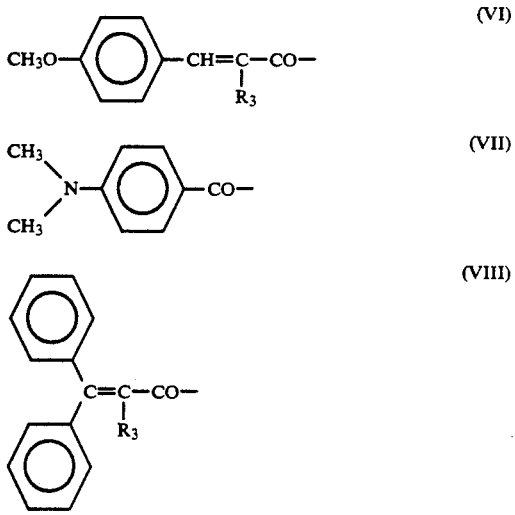

in which $R_3$ is hydrogen or the —CN group; to a process for the preparation thereof; to the use thereof in the preparation of compositions useful in cosmetics and dermatology; and to the dermatological compositions containing them.

It is now believed that the cause of the major part of the alterations which lead to ageing of the skin are to be attributed to the action of endogenic and exogenic free radicals. On this point, dermatology has in recent years increasingly concerned itself with the processes and causes which lead to the formation of these highly reactive chemical groups, with their toxic effects and with possible defence mechanisms.

Apart from some chemical agents such as pharmaceuticals, it is principally physical factors, such as heat, light, UV radiation, supersonic waves and ionising radiation, which lead to the formation of free radicals.

Owing to their high reactivity, free radicals are capable of reacting easily with other neighboring molecules, to generate further free radicals; a chain reaction thus takes place which continues to generate radicals until it is interrupted by combination with a chemical group which effects the formation of a stable molecule.

This mechanism explains the destructive action of free radicals: in fact, they can bind to the elements of the cell, such as the nucleus, the proteins and particularly the membrane; consequently, alterations which disturb the normal metabolism appear in the cells.

The adverse action of free radicals on the skin tissue consists in an attack on the cell membranes, which causes a degradation of the fibers in the connective tissue, such as collagen and elastin, which are responsible for the "tautness" and softness of young skin; the consequence is ageing of the skin, which manifests itself in the appearance of dryness, scaling and wrinkles.

In nature, there are scavengers or deactivators of free radicals; these are enzymes present in skin tissue, such as superoxide dismutase or catalase.

These are not always sufficient for total blocking of the free radicals present, which can then exert their devastating action on the skin tissue, which thus ages, losing its smooth and soft appearance.

A principal cause of the damage induced by free radicals appears to be the UV fraction of solar radiation, so that the first line of defence consists in finding protection against the noxious action of UV radiation.

For this purpose, particular compounds have proved effective, such as so-called sunscreens which are capable of absorbing in the UV region of sunlight, inhibiting or at least slowing down the damaging action thereof and consequently the ageing of the skin. Numerous substances have been studied and used in experiments as UV absorbers, and there is extensive patent literature in existence on this topic, wherein compounds belonging to different chemical classes and capable of absorbing radiation from 280 to 400 nm to a greater or lesser degree are proposed. Of these compounds, however, only relatively few have been demonstrated as being suitable for use in practice; these include the esters of p-methoxycinnamic acid and p-aminobenzoic acid, benzotriazoles and hydroxybenzophenones.

These compounds are used as sunscreens, mainly for the preparation of cosmetic formulations which are generally used on the beach or at high altitudes for protection from solar radiation.

Of course, sunscreens do not succeed in totally blocking the formation of free radicals, also because these can be caused by other factors, as has already been mentioned.

A second line of defence consists therefore in cancelling out the effects of UV radiation, that is to say in destroying or deactivating the free radicals which they have formed.

Again, a few substances have been proposed for this purpose as free radical deactivators, such as, for example, vitamin E, 6-hydroxy-2,5,7,8-tetramethylchroman-2-carboxylic acid, 13-cis-retinoic acid and 6-ethoxy-1,2-dihydro-2,2,4-trimethylquinoline. However, these have not proved to be very effective; the search for a satisfactory and really effective solution against solar radiation and the damaging effects caused thereby, and hence against skin ageing, is therefore still proceeding.

It has now been found that the compounds of the formula (I) have a surprising skin-protecting activity. In fact, such compounds are built up by condensation of a molecule of the general formula (A) having a free-radical deactivation activity and of a molecule of the general formula (U), capable of absorbing the radiation in the UV region of the spectrum of light.

The skin-protecting activity on the part of the compounds of the formula (I) is affected by means of two combined mechanisms of filtration of UV radiation, thereby inhibiting the generation of free radicals by the latter at the skin level, and deactivation of the free radicals which may have been generated by UV radiation which has not been totally filtered out, or by other endogenic or exogenic factors. This property has shown itself to be surprisingly superior to that to be expected from simple additivity of the known activities.

Therefore the present invention relates to the compounds of formula (I). Some of said compounds contain one or more chiral carbon atoms, therefore the invention also relates to the enantiomers and diastereoisomers of compounds (I) and to the mixtures thereof. Due to the presence of basic groups in compounds (I), the invention also relates to the addition salts of compounds (I) with both inorganic and organic acids, such as hydrohalogenic, sulfuric, formic, acetic, benzoic acids.

Compounds of formula (I) are prepared by reaction of the tetramethylpiperidine derivatives of formulae (X)-(XIII)

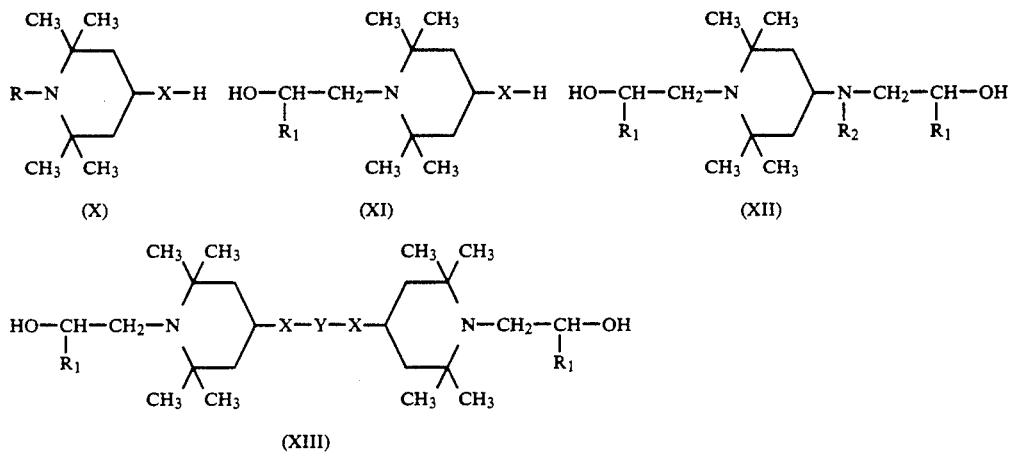

and the compounds of formula $R_4$—COZ, wherein $R_4CO$— represents the groups of formulae (VI)-(IX) and Z is OH, Cl, $OCH_3$ or $OC_2H_5$.

The condensation reaction can be carried out with methods known to those skilled in the art; the use of a solvent (organic or aqueous or a mixture thereof) as the reaction medium is uncritical, as far as it does not affect the progress of the reaction. Preferably the reaction is carried out in the absence of solvent. Catalysts promoting the reaction, such as tetrabutyl ortotitanate, can also be used.

Thanks to the advantageous characteristics of protecting action on the skin against the damages caused by UV radiations and free radicals, the compounds of the present invention can be used in the preparation of compositions for the dermatological use.

According to a preferred embodiment of the invention, the above compositions are used for the cosmetic treatment of the skin, and they can be in form of lotions, ointments, creams, emulsions, gels, oils, which are used as moisturizing, tonifying, detergent agents and particularly formulations protecting against solar radiation.

Preferably, these preparations are emulsions of the oil-in-water kind, and they can contain preservatives, emulsifiers, thickening agents, antioxidants, emollients, solvents, perfumes, dyes or other substances generally used in cosmetic compositions.

Generally the compositions, according to the present invention, can contain from 0.05 up to 10% and preferably from 0.1 to 5% of the compounds of formula I.

Of course the compounds of formula I can be added to the cosmetic compositions also together with other sunscreens and/or free radical deactivators.

The following examples illustrate the invention. Examples 1-10 relate to the preparation of compounds of formula (I), examples 11-14 concern the preparation of cosmetic compositions containing one compound of formula (I) as the active ingredient.

EXAMPLE 1

A mixture of 18 g of methyl p-dimethylaminobenzoate, 15.7 g of 2,2,6,6-tetramethyl-4-hydroxypiperidine and 0.2 ml tetrabutyl ortotitanate is heated and stirred for 6 hours at 170° C. The reaction product is recrystallized from petroleum ether at 100°/120° C. and decolourized with decolourizing earth.

4-(p-dimethylamino-benzoyloxy)-2,2,6,6-tetramethyl-piperidine is obtained in form of a crystalline white substance with m.p. 137°-139° C. and specific extinction (E:)—992 at 312 nm.

EXAMPLES 2-6

Following the same procedure of example 1, the compounds listed in table 1 are prepared.

TABLE 1

[Structure: R—N(piperidine with 4 CH₃ groups)—OOC—R₅]

| Ex. | R | R₅ | P.f. | E: | nm |
|---|---|---|---|---|---|
| 2 | $CH_3$ | (CH₃)₂N—C₆H₄— | 78-80 | 907 | 312 |
| 3 | H | $CH_3O$—C₆H₄—CH=C(CN)— | 100-102 | 892 | 342 |
| 4 | $CH_3$ | $CH_3O$—C₆H₄—CH=C(CN)— | 111-113 | 872 | 343 |
| 5 | H | $CH_3O$—C₆H₄—CH=CH— | 70-72 | 830 | 310 |
| 6 | $CH_3$ | $CH_3O$—C₆H₄—CH=CH— | 95-97 | 797 | 310 |

EXAMPLES 7-10

Following the same procedure of example 1, the compounds listed in table 2 are prepared.

TABLE 2

[Structure: $R_5$—COO—CH($R_1$)—CH₂—N(piperidine with 4 CH₃ groups)—OOC—$R_5$]

| Ex. | $R_1$ | $R_5$ | P.f. | E: | nm |
|---|---|---|---|---|---|
| 7 | H | (CH₃)₂N—C₆H₄— | 204-206 | 1267 | 315 |

TABLE 2-continued $$R_5-COO-CH(R_1)-CH_2-N\underset{CH_3\ CH_3}{\overset{CH_3\ CH_3}{\diagdown\diagup}}-OOC-R_5$$

| Ex. | R₁ | R₅ | P.f. | E: | nm |
| --- | --- | --- | --- | --- | --- |
| 8 | H | CH₃O—⟨○⟩—CH=CH— | 167–168 | 1021 | 310 |
| 9 | H | CH₃O—⟨○⟩—CH=C(CN)— | 177–179 | 1120 | 346 |
| 10 | C₂H₅ | CH₃O—⟨○⟩—CH=C(CN)— | 119–121 | 1066 | 341 |

EXAMPLE 11

Preparation of a Moisturizing Cream

A solution of 2 g of the compound of example 2 in 10 g of polyethylene glycol 400 is prepared heating to 60° C.; the resulting solution is added with 0.15 g of methyl paraben (methyl p-hydroxybenzoate) and 0.05 g of propyl paraben. Separately, a mixture of 15 g of vaseline and 8 g of glyceryl monostearate is prepared and added to the above obtained solution, at 80° C. After that, the oily phase is added with 63.8 g of water pre-heated at 80° C., under strong stirring, so as to obtain an emulsion, keeping stirring until temperature is decreased below 30° C.

EXAMPLE 12

Preparation of a Lipophilic Gel 6 g of high-melting paraffin and 3.6 g of sorbitan tristearate (Span 65 ®) are melted together and heated to 100° C.; the melted mixture is added, under strong stirring, to 77.9 g of vaseline oil pre-heated to 100° C., then it is quickly cooled to 50° C. to obtain a gel. This gel is added with a solution of 2.5 g of the compound of example 3 in 10 g of polyethylene glycol 400 previously prepared, mixing until homogeneity.

EXAMPLE 13

Preparation of a Sun Cream

A mixture of 10 g of cyclodimeticon/dimeticon copolymer (Dow Corning Q2-3225 C), 10 g of cyclometicon (Dow Corning 344), 0.5 g of polysorbate 20 (Tween 20 ®), and 6 g of the compound of example 6 is prepared. This mixture is added to a solution prepared previously, consisting of 0.2 g of 1,1'-methylene-bis-3-(3hydroxymethyl-2,4-dioxy-imidazolidinyl)urea, 0.05 g of methyl paraben and 73.25 g of water.

EXAMPLE 14

Preparation of a Face Make-Up

A mixture is prepared, heating to 75° C. 78.5 g of water, 4.5 g of glycerin, 0.6 g of 2-pyrrolidone-5-carboxylic acid and 0.2 g of methyl paraben. This mixture is added with a second mixture, prepared previously, consisting of 3 g of octyl palmitate, 1 g of dimeticon, 4.5 g of polysorbate 60 (Tween 60 ®), 0.1 g of propyl paraben, 7.5 g of glyceryl monostearate and 0.2 g of the compound of example 7.

I claim:

1. A compound selected from the group consisting of:
   4-(p-dimethylamino-benzoyloxy)-2,2,6,6-tetramethylpiperidine;
   4-(p-dimethylamino-benzoyloxy)-1,2,2,6,6,-pentamethylpiperidine;
   4-(p-methoxy-2-cyano-cinnamoyloxy)-2,2,6,6-tetramethylpiperidine;
   4-(p-methoxy-2-cyano-cinnamoyloxy)-1,2,2,6,6-pentamethylpiperidine;
   4-(p-methoxycinnamoyloxy)-2,2,6,6-tetramethylpiperidine;
   4-(p-methoxycinnamoyloxy)-1,2,2,6,6-pentamethylpiperidine;
   N-[2-(p-dimathylaminobenzoyloxy)ethyl]-4-(p-dimethylaminobenzoyloxy)-2,2,6,6-tetramethylpiperidine;
   N-[2-(p-methoxycinnamoyloxy)ethyl]-4-(p-methoxycinnamoyloxy)-2,2,6,6-tetramethylpiperidine;
   N-[2-(p-methoxy-2-cyano-cinnamoyloxy)ethyl]-4-(p-methoxy-2-cyano-cinnamoyloxy)-2,2,6,6-tetramethylpiperidine; and
   N-[2-(p-methoxy-2-cyano-cinnamoyloxy)butyl]-4-(p-methoxy-2-cyano-cinnamoyloxy)-2,2,6,6-tetramethylpiperidine.

2. A composition for use in stabilizing polymers comprising at least one of the compounds according to claim 1.

* * * * *